United States Patent [19]

Schrader

[11] Patent Number: 4,474,929

[45] Date of Patent: Oct. 2, 1984

[54] POLYGLYCIDYL ETHERS OF BRANCHED NOVOLACS

[75] Inventor: Paul G. Schrader, Antioch, Calif.

[73] Assignee: The Dow Chemical Company, Midland, Mich.

[21] Appl. No.: 538,033

[22] Filed: Sep. 30, 1983

[51] Int. Cl.$^3$ .................. C08G 8/36; C08G 59/32
[52] U.S. Cl. .................. 525/482; 525/480; 525/481; 525/491; 525/507; 528/98
[58] Field of Search .............. 525/480, 482, 507, 481, 525/491; 528/98

[56] References Cited

U.S. PATENT DOCUMENTS

| | | | |
|---|---|---|---|
| 2,801,989 | 8/1957 | Farnham | 528/98 |
| 3,483,164 | 12/1969 | Barton et al. | 528/98 |
| 4,079,113 | 3/1978 | Kimura et al. | 525/507 X |
| 4,102,866 | 7/1978 | Speranza et al. | 525/507 |
| 4,137,220 | 1/1979 | Lazzerini et al. | 525/507 |
| 4,256,844 | 3/1981 | Martin et al. | 525/507 X |
| 4,342,852 | 8/1982 | Takeda et al. | 525/501 X |
| 4,345,054 | 8/1982 | Takeda et al. | 525/503 X |
| 4,368,298 | 1/1983 | Okayama et al. | 525/507 X |
| 4,390,664 | 6/1983 | Kanayama | 525/482 X |
| 4,394,496 | 7/1983 | Schrader | 528/98 |

*Primary Examiner*—Howard E. Schain
*Attorney, Agent, or Firm*—Robert R. Stringham

[57] ABSTRACT

Branched epoxy novolacs having from 5 to 10 (or more) glycidyl ether groups per molecule are prepared by the epoxidation of novolacs made by the reaction of mono- or dihydric phenols with mono- or dinuclear diphenols ring-substituted with 3- or 4-methylol and/or alkoxymethyl groups.

6 Claims, No Drawings

POLYGLYCIDYL ETHERS OF BRANCHED NOVOLACS

BACKGROUND OF THE INVENTION

Novolacs, the acid-catalyzed condensation products of phenols with less than 1 mole of formaldehyde per mole of phenol, constitute a well-known class of phenolic resins and have found wide use. The novolacs in commercial use are derived preponderantly from mononuclear, monohydric phenols, such as phenol itself, cresol, p-t-butylphenol, octyphenol and xylenol. Large amounts of resorcinol, a mononuclear, dihydric phenol, are also used, however, in novolac manufacture.

A relatively recently developed novolac is derived from bisphenol A and contains eight aromatic nuclei (benzene rings), each having a phenolic hydroxyl attached to it. This novolac is marketed by Celanese Corporation in the form of its octaglycidyl ether, a high molecular weight epoxy resin known by the tradename "SU-8". The (unadvanced) novolac may be represented by the following ideal structure:

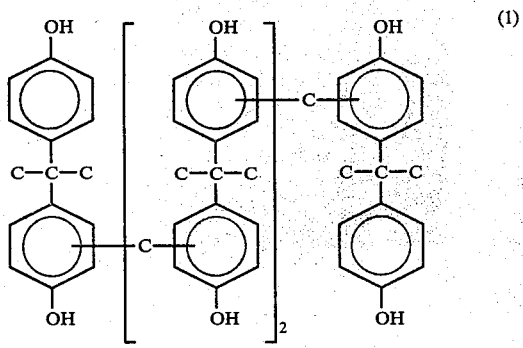

It will be seen that the novolac of formula (1) is actually linear in structure, i.e., is not branched.

SU-8 is a hard, high melting epoxy resin which reacts rapidly, has good heat resistance and cold-flows to a lesser extent than more conventional high molecular weight epoxy novolacs. However, it not only is brittle but also contains low molecular weight epoxide species derived from the free bisphenol inevitably present in novolacs prepared by the reaction of formaldehyde with bisphenols. The latter species are present in sufficient amount so that the epoxy will still cold flow, albeit to a limited extent. Also inevitably present in conventional bisphenol novolacs are species of sufficiently high molecular weight to undesirably increase the gelling speed of the "epoxidized" novolac.

Thus, it is clear that a method of making bisphenol-derived novolacs which largely retain the advantages but not the disadvantages of the novolac precursor to SU-8 would be highly desirable.

OBJECTS OF THE INVENTION

The primary object of the present invention is to provide bisphenol-derived, epoxy novolac formulations which exhibit little or no tendency either to cold flow (as the cured resins) or to gel prematurely.

Another object is to provide bisphenol-derived epoxy novolacs which have a somewhat lower functionality than SU-8 but consist of more compact molecules and, when cured, are not hard or brittle.

An additional object is to provide compact, relatively low molecular weight epoxides having up to 10 or more glycidyl ether groups per molecule.

Yet another object is to provide epoxies which are of the foregoing type except for being derived from dihydric mononuclear phenols (dihydroxy benzenes, for example).

A further object is to provide a method of preparing such epoxides which affords a narrower molecular weight range but with considerable latitude as to average molecular weight.

Still other objects will be made apparent to those knowledgeable in the art by the following specifications and claims.

SUMMARY OF THE INVENTION

It has been discovered that the foregoing objects can be achieved by "epoxidizing" novolacs prepared from difunctional phenols ring-substituted with three or four methylol and/or alkoxymethyl groups. The precursor novolacs are prepared by reacting the substituted phenol in the presence of an acid with a mono- or diphenol to convert the methylol and/or alkoxymethyl groups to mono- or dihydroxybenzyl groups. A typical novolac produced by this method is derived from tetramethylol bisphenol A and ordinary phenol. When prepared at phenol to methylol ratios of about 5 or more, it can be represented by the following formula:

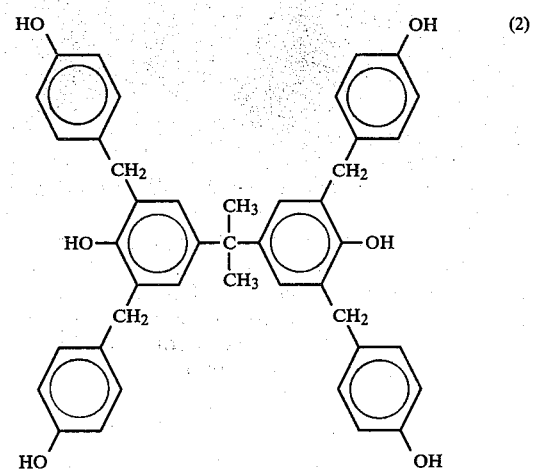

The most preferred method of preparing the novolacs is a "one-pot" process which includes, as a first step, preparation of a poly(methylol- and/or alkoxymethyl) dihydric phenol, by whatever method, as a precursor to the novolac.

It will be seen that the hexaglycidyl ether of the latter novolac will have a branched, rather than a linear structure and will accordingly provide a more closely knit structure than SU-8.

Definitions of Terms

As used herein, "difunctional phenol" includes both dinuclear diphenols ("bisphenols") and mononuclear diphenols (simply "diphenols" hereinafter).

The term "poly(methylol and/or alkoxymethyl)-difunctional phenol" as used herein is intended to denote a bis- or diphenol ring substituted with at least three methylol and/or alkoxymethyl groups.

The term "alkoxymethyl" as used herein denotes a monovalent radical of the formula R—O—CH₂ — in which R is an alkyl, aralkyl or cycloalkyl group of from 1 to 30 carbons, preferably a 1 to 4 carbon alkyl group.

The term "methylol- or alkoxymethyl-reactive phenol" is used herein to denote a mono- or dihydric phenol having at least one ring hydrogen capable of condensing with a methylol or alkoxymethyl group—attached directly to a hydroxy-substituted benzene ring—to eliminate a molecule of water or of the corresponding alcohol, R—OH (R being defined as above).

The term "epoxidize" means to form the polyglycidyl ether of the novolac.

The Invention Defined

The method of the present invention may be broadly defined as the method of preparing an epoxy novolac which comprises epoxidizing a novolac prepared by reacting a poly(methylol and/or alkoxymethyl)difunctional phenol with at least one molecular proportion of a methylol- and/or methoxymethyl-reactive phenol per methylol (etc.) group, in the presence of an acidic catalyst for the reaction of active ring hydrogens with the methylol and/or alkoxymethyl groups.

The epoxides of the present invention may be broadly defined as products of the foregoing method of the invention. Preferred such products are those derived from phenol itself and from p,p' bisphenols substituted with a methylol or alkoxymethyl group in each of the four ortho positions therein.

DETAILED DESCRIPTION OF THE INVENTION

Suitable Reactants for the Preparation of the Precursor Novolacs

The formaldehyde may be provided in the form of any suitable formaldehyde source material, such as, for example, formalin, paraformaldehyde or s-trioxane.

Suitable polymethylol difunctional phenols for use, as such or as precursors to corresponding alkoxymethyl derivatives, in the method of the present invention are bis- or diphenols ring-substituted with at least 3—preferably 4—methylol groups. Otherwise unsubstituted phenols, such as tetramethylol hydroquinone or tetramethylol bisphenols of the formula

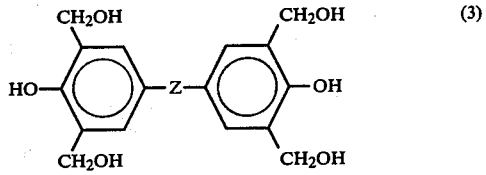

(3)

wherein —Z— is a valence bond, a C₁-C₄ alkylene or alkenylene group or a =C(CF₃), —CO—, —O—, —S—, —SO— or —SO₂— group,
are more preferred. However bisphenols having four active hydrogens can be prepared from meta-substituted phenols—such as m—cresol, for example—and, at least as the p,p' isomers, can be converted to the tetramethylol derivatives.

It is generally preferred that the bisphenol employed consists 100% of the p,p' isomer ("para Bis A", for example). However, the presence of minor amounts of the o,p' isomer (as in "ER Bis A"—97% p,p' and 3% o,p'—for example) is not necessarily detrimental. In fact, assuming that all three active hydrogens in the o,p' isomers can be replaced by methylol groups, the latter isomers may be preferred for the preparation of trimethylol bisphenols.

For the purposes of the present invention, the polymethylol compound preparations are generally carried out by allowing from about 30 to 120 minutes for formation of the bis-phenate slurry and then reacting it for about 2 to 4 hours with a 5–10% excess of the formaldehyde source material at temperatures within the range of from about 50°–70° C. (60° C., preferably).

It should be noted that pure trimethylol bisphenols may be somewhat difficult to prepare simply by the standard base-catalyzed reaction of the unsubstituted diphenols or p,p'-bisphenols with an excess of formaldehyde. That is, they may be obtained only in admixture with di- and/or tetramethylol derivatives. The content of the trimethylol compounds in such mixtures may be increased by using little or no excess of formaldehyde, employing bases which are less effective catalysts than NaOH and by terminating the reaction short of completion. (As a general proposition, this will be done only when a novolac having an average functionality of less than 6 is desired).

When the presence of one non-(methylol or alkoxymethyl) group in a tri(methylol and/or alkoxymethyl)-dihydric phenol is tolerable or desirable, the trimethylol derivative can more readily be prepared (so long as said group does not interfere, i.e., does not excessively deactivate the ring hydrogens expected to react with the formaldehyde).

That is, unsymmetrical bisphenols having the single substituent in a position ortho (or para) to one of the two phenol groups may be reacted with an excess of formaldehyde under somewhat more severe conditions than those used for the preparation of tetramethylol derivatives of unsubstituted bisphenols. (The requisite monosubstituted bisphenol starting material may be prepared either by direct substitution in the bisphenol or by reacting an aldehyde or ketone with a mixture of substituted and unsubstituted phenols in proportions appropriate to their relative reactivities, and then isolating the desired monosubstituted bisphenol, as by preparative chromatography.)

If the dihydric phenol is resorcinol, one of the ring hydrogens will be meta to both hydroxyls and should be substantially less reactive than the other three ring hydrogens. Thus, with care, the trimethylol derivative should be directly preparable. However, in both catechol and quinol (hydroquinone) all four ring hydrogens are reactive and monosubstitution with a non-interfering group is advisable if a trimethylol derivative of either of these diphenols is desired. Exemplary of substituent groups known or believed to be essentially non-interfering are C₁-C₂₀ alkoxy or alkenyloxy, C₁-C₂₀ alkyl, alkenyl, cycloalkyl or cycloalkenyl groups, and phenyl, benzyl, halo and nitro groups.

It is well within the skill of the art to determine whether any particular substituent in a given position with respect to the phenolic hydroxyl(s) will prevent the introduction of at least three methyol groups in a given difunctional phenol. Some guidance in this respect will be found in *ACS Monograph* (No. 98): Formaldehyde. J. F. Walker. Reinhold Pub. Corp., N.Y. (1944), Ch. 10, pp. 167–172. Reference may also be had to the numerous texts on organic chemistry which include discussions of the influences of various substituents on the chemistry of phenols, benzyl alcohol, etc.

Reference may also be had to U.S. Pat. No. 4,256,844 and to the patents cited therein.

It is likewise well within the skill of the art to determine whether or not a given mono- or dihydric phenol is methylol- or alkoxymethyl-reactive. This does not necessarily require testing the phenol with the polymethylol (etc.) difunctional phenol to be used. If the candidate phenol will condense—for example—with the methylol group(s) in saligenin (o-hydroxybenzyl alcohol), 2,4- or 2,6-dimethylol phenol or 2,4,6-trimethylolphenol, it should be suitable as a "methylol reactive phenol" for the practice of the present invention. Other methylol-substituted monophenols which may be more representative of particular polymethylol difunctional phenols are monomethylol xylenols, the 2,6-dimethylol derivative of p-benzylphenol, the dimethylol derivatives of o-chlorophenol and 2-nitro-4-methylolphenol. The corresponding methoxymethyl derivatives of the foregoing methylol-substituted monophenols may similarly be used to test for the requisite reactivity of a candidate alkoxymethyl-reactive phenol.

Representative tetramethylol difunctional phenols are tetramethylol bisphenol A and tetramethylol hydroquinone. By reaction with a several fold excess of phenol or a dihydroxy benzene, the latter, tetramethylol compound (or the corresponding mono- to tetraalkoxy derivatives thereof) may be converted to novolacs, for use in the present invention, having the following formula:

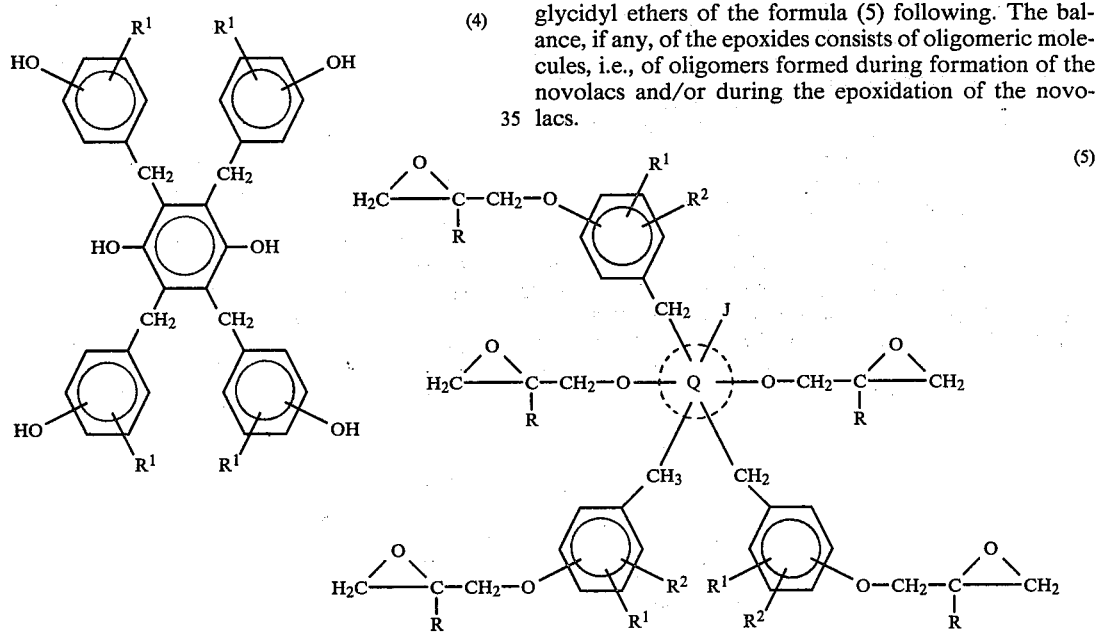

wherein $R^1$ is H or p-OH (the same in each occurrence, unless a mixture of mono- and diphenols is used).

It will be seen that novolacs of the latter formula are not only branched but are even more compact than those of formula (2). If $R^1$ is —OH in each occurence, the novolac has a phenolic hydroxyl functionality of 10.

If the methylol- or alkoxymethyl-reactive phenol used is a substituted monophenol, such as, for example, a cresol, guiacol or anole (phenol substituted in the para position with —CH=CH—CH$_3$), the novolac has the ideal structure shown in formula (4), except that $R^1$ is CH$_3$, o—CH$_3$O— or p(—C=CH—CH$_3$), etc., respectively The presence of the substituent in a position ortho to a phenolic hydroxyl is preferred.

Those knowledgeable in the art will recognize that novolacs of either of formulas (2) or (4) should be amenable to ring-substitution with halo- or nitro groups (either of which should increase the reactivities of the phenolic hydroxyl groups). This would also be true of novolacs like those of formulas (2) or (4) but derived from mono- or dihydric phenols monosubstituted with alkyl, alkenyl, alkoxy groups, etc.

As indicated earlier herein, the poly(methylol and/or alkoxymethyl)dihydric phenol from which the novolac is derived may be made from a similarly substituted difunctional phenol.

Generic Epoxy Novolac Formula

The epoxy novolacs of the present invention consist at least partially of the monomeric, polynuclear, polyglycidyl ethers of the formula (5) following. The balance, if any, of the epoxides consists of oligomeric molecules, i.e., of oligomers formed during formation of the novolacs and/or during the epoxidation of the novolacs.

wherein:
R is H or CH$_3$,
$R^1$ is H, a C$_1$-C$_{20}$ alkyl, alkenyl, cycloalkyl, cycloalkenyl, aralkyl, aralkenyl, aryl, alkaryl, alkenylaryl, alkoxy or alkenyloxy group or a halo or nitro group, independently in each occurrence,
$R^2$ is H or OH, independently in each occurrence,
J is H, and $R^1$ group as above-defined or is a fourth

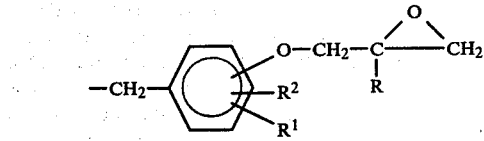

group, and

Q is the residue of a poly(methylol and/or alkoxymethyl) difunctional phenol of either of the following formulas:

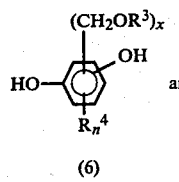 and 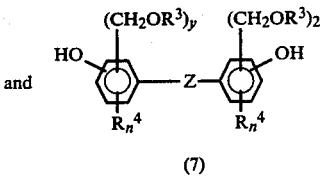

(6)            (7)

in which $R^4$ is defined as is $R^1$ above, x is 3 or 4, n is 0 or 1, y is 1 or 2, —Z— is a valence bond, a $C_1$-$C_4$ alkylene or alkenylene group, or a $=C(CF_3)_2$, —CO—, —O—, —S—, —SO— or —$SO_2$— group and $R^3$-independently in each occurrence is H or a $C_1$-$C_{30}$ alkyl, aralkyl or cycloalkyl group.

It is not possible to represent the oligomeric epoxy novolacs of the invention by a single, ideal formula. It is believed that oligomerization during novolac formation involves reaction of methylol groups with methylol or alkoxymethyl groups in different molecules and reaction of more than one ring hydrogen in a reactive phenol molecule with as many methylol (or, to a lesser extent, alkoxymethyl) groups in different molecules. (Formation to two —$CH_2$— links between a reactive phenol molecule and a polymethylol (etc.) dihydric phenol molecule appears possible, but less probable and would not result in oligomerization.) Thus, the oligomeric novolacs of the invention are believed to include "abnormal" linkages such as are shown in the following segment hypothesized for a novolac derived from tetramethylol hydroquinone and phenol. (It will be noted that such segments may contain substantially more than 10 phenolic hydroxyls.)

methylol groups on the same aromatic ring. To the extent that this occurs, the phenolic equivalent weight of the novolac may be raised other than by oligomerization. That is, this reaction would result in a molecular weight decrease, rather than increase. Reaction of an alkoxymethyl group with an adjacent methylol group is less likely but appears possible—at least when the alkoxymethyl group is a methoxymethyl group. However, interaction of two adjacent alkoxymethyl groups is improbable and this is another advantage of poly(alkoxymethyl) diphenols as novolac precursors.

Such oligomerization as occurs during epoxidation will result from adduction of otherwise unconverted phenolic hydroxyls with oxirane groups in established glycidyl ether groups. That is, "advancement" to a higher molecular weight exposy resin may occur. Any undesired tendency in this direction can generally be suppressed by employing a higher epichlorohydrin (or methylepichlorohydrin) to phenolic hydroxyl ratio in the epoxidation mixture, as is illustrated subsequently herein.

Preparation of the Precursor, Branched Novolac

The methyol- and/or alkoxymethyl-substituted diphenol may be pre-prepared or made in situ. The alkoxymethyl-containing species are conveniently made from the tri- or tetramethylol compounds by reaction of the latter with an excess of an alkanol or cycloalkanol in the presence of an acid catalyst in a manner similar to that employed in converting the methylol derivatives to the novolacs used in the invention. The alkoxymethyl compounds are substantially less reactive than the methylol compounds but this is actually an advantage. The polymethylol compounds must be stored in a freezer (and even then self-react, albeit slowly) whereas the poly(alkoxymethyl) compounds are stable—but still reactive enough to be used to make the novolacs.

In one procedure for novolac preparation, the basic methylolation mixture is carefully neutralized with $CO_2$ (under pressure) or a dilute mineral acid, such as 3N HCl and is then made just slightly acid (with dilute HCl, for example). The resulting brine layer is separated and a methylol-reactive mono- or dihydric phenol (or an alcohol) is mixed with the organic phase before the catalytic acid is added. If an alcohol is to be reacted with the —$CH_2OH$ groups, the mixture (or the separate components thereof) should also be dried first.

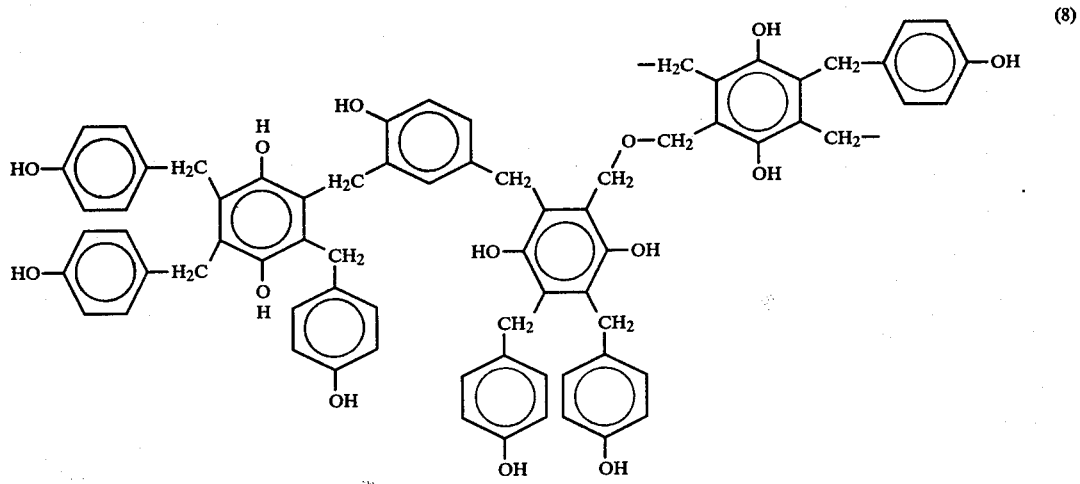

(8)

The novolacs may also include some —$CH_2OCH_2$— groups formed by intramolecular reactions of adjacent It should be noted that the preceding neutralization must be done with an acid which is weak (but stronger than phenol) or is dilute; that is, even moderately concentrated mineral acids strongly catalyze methylol/methylol interaction.

A considerably less "touchy" situation results if the methylol-reactive phenol is mixed with the basic methylolation mixture before it is neutralized. In this case, a strong acid (such as 12N HCl) can be used for the neutralization. However, this alternative results in the presence of some of the phenol—a pollutant—in the aqueous brine which must be separated and disposed of after the novolac-forming reaction is complete.

Due to the lower reactivity of alkoxymethyl groups, addition of the catalyst for the preparation of a novolac from a tri- or tetra(alkoxymethyl)diphenol (preformed or made in situ) is not a problem.

Suitable acids for catalysis of the novolac-forming reaction include those, such as oxalic acid, for example, generally used in the preparation of conventional novolacs (from HCHO and phenols). HCl is convenient but acids such as p-toluene sulfonic acid, oxalic acid or acid-form ion exchange resins are also suitable. The amount of acid introduced as the condensation catalyst should be at least enough to lower the pH to about 1.0. Greater amounts of (anhydrous) acids tend to complex the water eliminated in the condensation but are not otherwise beneficial.

The methylol-reactive phenol should be employed in the amount of at least 1 molecular proportion per methylol or alkoxymethyl group to be reacted out. At low ratios (~1–1.5) the novolac produced will generally be predominantly oligomeric and will have a relatively high molecular weight. A high purity monomeric novolac having the ideal structure of formula (5) can be obtained with phenol itself at phenol/—CH$_2$OH ratios of about 8–10 (mole ratios of about 36:1 to 40:1 for a tetramethylol difunctional phenol). Even higher ratios can be used, but to little or no advantage. "Monomeric" novolacs containing only minor amounts of oligomers can be obtained at ratios of from about 2.0 to 7.5 depending on the relative reactivities of the phenol and the methylol groups, the reaction temperature and the method of combining the reactants.

In general, however, substantial oligomer contents will result at ratios of about 5 or less, particularly when the method of reactant combination employed in Example IV-A herein is used.

The novolacs low in oligomers are soft. The predominantly oligomeric novolacs are hard.

Another advantage of using poly(alkoxymethyl) diphenols is that self-reaction is considerably less of a problem and substantially less oligomerization should result at a given phenol/reactive-group ratio. That is, essentially monomeric novolacs should be preparable from most phenols at ratios as low as 2.5, even when employing the reactant combination method of Example IV-A.

Those novolacs used in the practice of the invention having really high contents of oligomeric products generally have higher average molecular weight ranges that are desirable for most used they would find in the form of their epoxidized derivatives. Accordingly, novolacs made at phenol to methylol ratios of at least 2.5 are preferred as epoxy resin precursors. The novolacs obtained from phenol per se at ratios in the range of about 2 to 3 molecules of phenol per methylol group are more preferred, by reason of providing epoxides (poly- glycidyl ethers) of sufficient hardness to be non-sintering, yet low enough in melt viscosity to give good flow properties in molding "compounds". When the phenol is cresol, ratios of about 2.5 to 5.0 are preferred.

Some polymethylol difunctional phenols—such as tetramethylol bisphenol A, for example—tend strongly to crystallize and are most easily utilized when made in situ and mixed with the methylol-reactive phenol immediately after the brine layer has been removed. This is also advantageous in drastically reducing the rate of self-reaction on the part of highly reactive methylol compounds. Further, it is essential to pre-mix the reactants before the catalyst is introduced because self-reaction of the methylol compounds is inherently faster than the desired reaction of methylol groups with ring hydrogens and both reactions are speeded up by the catalyst.

The methylol/phenol reaction may be started by slightly warming the catalyst-containing mixture of reactants but, once under way, is very exothermic. After the rate of reaction drops off, however, the mixture is heated (at reflux, conveniently) for an arbitrary period of from one to several hours, to ensure completion of the reaction. Less of an exotherm would be expected when at least one of the methylol groups has first been converted to an alkoxymethyl group.

Suitable reaction temperatures for the novolac-forming condensation extend from the lowest temperature at which adequate stirring and a practical reaction rate can be attained to the highest temperature at which the extent of side-reaction and/or degradation is not intolerable. In general, however, temperatures—including the peak temperature allowed during the exotherm—within the range of from about 40° to about 70° C. are preferred when the methylol—or alkoxymethyl-reactive phenol is phenol itself. When the phenol is a cresol, temperatures within the range from about 60° to about 107° C. are preferred.

Replacement of methylol groups in a polymethylol diphenol by alkoxymethyl groups is done in a closely similar manner to novolac preparation. However, if conversion of a high proportion of the methylol groups is desired, it is essential to minimize the water content of the reactants. Thus, for example, any separate aqueous phase present is separated as completely as possible from the polymethylol compound, which is then taken up in a suitable alcohol, dried by azeotroping and—if a different alcohol is to be reacted with the methylol groups, is stripped in a rotary evaporator in vacuo and taken up in the latter (pre-dried) alcohol. Otherwise, sufficient of the azeotroping alcohol can be charged initially to leave enough for the reaction after azeotroping is complete. The acid catalyst is either concentrated (c HCl, for example) or anhydrous. The reactant/catalyst mixture is then stirred at a temperature of about 65° to 80° C. for at least several hours. When methanol—the most preferred alcohol—is used, the reaction mixture is refluxed for as long as 10 hours (or more) when a high degree of conversion of —CH$_2$OH to —CH$_2$OCH$_3$ groups is desired.

If conversion of only a portion of the —CH$_2$OH groups is desired, the alcohol concentration is reduced, as by dissolution of an inert solvent, and/or the contact time and/or reaction temperature is reduced.

The reaction mixture may be worked up for the novolac in any suitable manner. A simple and effective workup is to neutralize the acid with 50% aq. NaOH, separate the resulting brine, strip off most of the unconverted methylol- or alkoxymethyl-reactive phenol in a rotary evaporator under reduced pressure, complete phenol removal by steam stripping and dry the residual product in a rotary evaporator under reduced pressure—allowing the final pot temperature to reach about 150° C. (At such elevated temperature, the novolac produced can be removed from the vessel—usually with the aid of a hot-air gun—as a viscous but flowable melt.)

The Epoxidation Procedure

The process aspect of the present invention resides in the novelty of the novolacs utilized for the preparation of the epoxides, not in how the epoxidation is carried out. (The novolas, per se, and the method by which they are prepared, are claimed in a separate application of the present inventor.) Thus, the present process invention may be defined as the method of preparing a polyglycidyl ether of the foregoing structure (5) which comprises reacting the corresponding novolac with an epihalohydrin of the formula

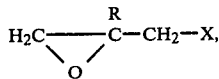

in which, independently in each occurrence, R is H or $CH_3$ and X is Cl or Br.

Preferably, the epihalohydrin is epichlorohydrin and the first step of the epoxidation—coupling, or —OH-/oxirane adduction—is catalyzed with a "quat" such as BTMAC (benzyl, trimethylammonium chloride). However, as illustrated in the examples herein, the same base employed for dehydrohalogenation of the coupling product may also be employed to effect coupling.

The molecular weight of the epoxide can be controlled not only by manipulating reactant ratios (in the novolac and epoxide-forming steps) but also by the choice of the methylol-reactive ("capping") phenol used. That is, "fine tuning" of molecular weight-dependent properties may be achieved by selecting alkyl substituted phenols (ortho-alkyl phenols, preferably) in which the size of the alkyl group is larger or smaller. Also, the proportion of the alkyl phenol in mixtures of the same with ordinary phenol can be varied.

EXAMPLES

The following examples are for purposes of illustration and are not to be construed as limiting the present invention in a manner inconsistent with the claims appended to these specifications.

EXAMPLE I

Preparations and epoxidations of novolac from bisphenol A and phenol.

Step 1

100 Grams (0.438 gram moles) of bisphenol A flakes were stirred with 200 ml of deionized water in a 500 ml three-neck, round-bottom flask and 70 grams of 50% NaOH (0.875 g moles) was added, resulting in an exotherm to 36° C. and formation of a thick, white slurry. After the slurry had been stirred ½ hour, 146 grams of formalin solution (1.8 g moles HCHO) was added and the slurry then gradually altered to a clear solution. The solution was heated to 40° C. and stirred at that temperature overnight. 1.06% of the formaldehyde remained unconverted.

Step 2

The reaction mixture was transferred to a 2-liter, 3-neck flask and there was added 457 grams of "liquid phenol"—90% phenol, 10% water (4.37 g moles of phenol; ~2.5 moles per —$CH_2OH$). The mixture was neutralized with 72 ml of 12N HCl and another 28 ml. of the acid was added as a catalyst, the acidified mixture was then refluxed, with stirring, for 1½ hours, neutralized with 50% NaOH and made acid with acetic acid. The resulting brine layer was separated and the organic phase freed of phenol by steam stripping to a final pot temperature of 150° C. The stripped residue weighed 278 grams (97.3% of theoretical for the desired 6-functional novolac) and therefore was presumed to consist essentially of the monomeric novolac of formula (2) herein.

Step 3

When 275 grams (0.4217 g moles) of the novolac were "epoxidized" by treatment with 25.29 g moles (~10 moles per phenolic OH) of epichlorohydrin (see following description of procedure) there was obtained 422 grams (vs 416.5 grams theoretical yeild) of a straw-colored, semi-solid resin having an EEW (epoxide equivalent weight) of 178 (vs 164.8, theoretical).

Epoxides of the type made in Run 1 have Mettler softening (dropping) points of about 60°-70° C. and melt viscosities of about 240 centistokes at 150° C. (Brookfield HAT microviscometer).

The epoxidation was carried out by the following procedure. The novolac was stirred in a 2-liter, 3-neck, round-bottom flask with the epi (epichlorohydrin). 2.8 Grams of 60% benzyltrimethylammonium chloride was added as a coupling catalyst to the resulting solution, which was refluxed for one hour and then cooled to 25° C. Dehydrochlorination was done in two steps, the first step being mainly dehydrochlorination of the glycerine dichlorohydrin present after the coupling reaction. 222.6 Grams of 25% aq. NaOH was slowly added to the solution at 25°. Stirring was continued for 30 minutes more and then the epichlorohydrin was stripped out in a rotary evaporator, leaving the salt from the first dehydrochlorination in the resin. The resin was taken up in 100 ml of a 75/25 mixture of MEK (methyl ethyl ketone) and toluene and transferred back to the 2-liter reaction flask, together with a rinse of the evaporator with a little more MEK/toluene. The flask was fitted with a stirrer, thermometer, reflux condenser and dropping funnel. The contents were heated with stirring to 60° C. and addition of another 222.6 gram portion of 25% NaOH commenced. The addition was completed over a period of one hour while holding the temperature at about 60°. After stirring was continued at the latter temperature for another hour, 200 ml more of 75/25 MEK/toluene and 100 ml of deionized water were added. A brine separated cleanly and readily and was removed. The resin solution was dried with anhyd. $MgSO_4$ (but could have been dried by azeotroping out the water) and was filtered. The solvent was stripped off (again, in a rotary evaporator) to leave the resinous epoxide (nominally, the hexaglycidyl ether of the novolac).

The effects on epoxide properties of certain parameters of the novolac preparation process are significant.

(These effects are of course in addition to the usual effects of the variables in the epoxidation step itself.)

The following Table I is a compilation of data for twelve, 3-step epoxide preparations (Runs 2-13)—starting from bisphenol A and using phenol to cap the tetramethylol compound. The preparations were carried out essentially in the manner of the preceding example but at various phenol to methylol ratios and epi to novolac ratios. Also, two different methods of achieving coupling and dehydrochlorination were used in carrying out the epoxidations, as indicated in the Table.

It will be seen from the Table that small differences in the phenol to methylol ratio (as between Runs 8 and 12—which were otherwise essentially identical) can make a considerable difference in the melt viscosity of the epoxides derived from the resulting novolacs. It will also be seen that the stoichiometries employed in Run 13 (phenol/—CH$_2$OH ratio=2.5 and epi/phenolic —OH ratio=5) gave a melt viscosity of 630 centistokes, which is just about right for molding applications.

An indication of the relative effects on EEW of low phenol to methylol ratios and low epi to phenolic OH ratios is apparent from a comparison of Runs 3, 10, 11 and 13.

TABLE I
PREPARATIONS OF NOMINALLY SIX-FUNCTIONAL NOVOLAC EPOXIDES

| Run No. | Phenol/ Methylol Ratio | Epi to Phenolic OH Ratio | Coupled with | Dehydro- chlorinated with | EEW | Hyd. Cl %[4] | Mettler S.P. of Epoxide | Melt Viscosity 150° C. Cks |
|---|---|---|---|---|---|---|---|---|
| 2 | 2.5/1 | 10/1 | BTMAC | NaOH/Na$_2$CO$_3$ | 178 | | Soft | |
| 3 | 2.5/1 | 2/1 | " | " | 256 | | | 1393 cks. |
| 4 | 1.5/1 | 10/1 | " | " | 226 | | | |
| 5 | 1.25/1 | 10/1 | " | " | 219 | 2.24 | 90.9° | |
| 6 | 1.5/1 | 10/1 | " | 25% NaOH in MEK—toluene | 216 | 0.08 | 87° | |
| 7 | 2/1[1] | 10/1 | " | NaOH—MEK—tol. | 214 | 0.16 | 88.2° | 2787 cks. |
| 8 | 2/1[2] | 10/1 | " | " | 214 | 0.11 | 92.5° | 3139 cks. |
| 9 | 5/1 | 10/1 | " | " | 194 | | Soft | |
| 10 | 5/1 | 1.2/1 | NaOH only | " | 294 | | 87.2° | |
| 11 | 5/1 | 1.3/1 | " | " | 294 | | | |
| 12 | 2.5/1 | 10/1 | BTMAC | " | 201 | 0.37 | 66.6° | 241 cks. |
| 13 | 2.5/1 | 5/1 | " | " | 212 | 0.06 | 77.1° | 630 cks. |

NOTES:
[1]Mettler softening point of novolac 124.1° C.
[2]Mettler softening point of novolac 114.6° C.
[3]Benzyltrimethylammonium chloride.
[4]Hydrolyzeable chloride in epoxide.

TABLE II
SIX FUNCTIONAL NOVOLAC FORMATIONS CURED 2 HRS./100° + 18 HRS./180° C.

| Formulation No. | Curing Agent | Amount[5] | HDT[6] °C. | Flex. Strength | Flex. Modulus | Barcol Hardness |
|---|---|---|---|---|---|---|
| 530 | MDA[1] | 0.5 | 156 | 11,100 | 550,000 | 49 |
| 531 | " | 0.7 | 280 | 14,400 | 492,000 | 48 |
| 532 | " | 0.9 | 252 | 15,500 | 497,000 | 48 |
| 533 | " | 1.1 | 255 | 11,100 | 477,000 | 47 |
| 534 | " | 1.5 | 239 | 9,670 | 538,000 | 50 |
| 535 | m-PDA[2] | 0.5 | 355 | 12,500 | 543,000 | 51 |
| 536 | " | 0.7 | 195 | 13,400 | 530,000 | |
| 537 | " | 0.9 | 216 | 5,170 | 546,000 | |
| 538 | " | 1.1 | 233 | 11,000 | 548,000 | |
| 539 | " | 1.5 | 232 | 6,220 | 498,000 | |
| 540 | NMA[3] + 2% BDMA[4] | 0.5 | 173 | 13,700 | 515,000 | |
| 541 | NMA[3] + 2% BDMA[4] | 0.7 | 204 | 16,400 | 491,000 | |
| 542 | NMA[3] + 2% BDMA[4] | 0.8 | 219 | 16,100 | 518,000 | |
| 543 | NMA[3] + 2% BDMA[4] | 0.9 | 224 | 9,790 | 526,000 | |
| 544 | NMA[3] + 2% BDMA[4] | 1.0 | 202 | 12,400 | 525,000 | |
| 545 | NMA[3] + 2% BDMA[4] | 1.1 | 191 | 8,600 | 554,000 | |
| 546 | NMA[3] + 2% BDMA[4] | 1.5 | 148 | 13,800 | 468,000 | |
| SU-8 EEW | NMA[3] + 2% | 0.7 | 220 | 14,600 | 490,000 | |

Example II

Properties of the epoxide of Run 2, Example I, when cured with successively greater amounts of different curing agents.

The epoxy novolac made in Run 2 was formulated and cured as indicated in the following Table II. For comparison, data are also given for the commercial epoxy resin, SU-8.

TABLE II-continued
SIX FUNCTIONAL NOVOLAC FORMATIONS CURED 2 HRS./100° + 18 HRS./180° C.

| Formulation No. | Curing Agent | Amount[5] | HDT[6] °C. | Flex. Strength | Flex. Modulus | Barcol Hardness |
|---|---|---|---|---|---|---|
| 234 | BDMA[4] | | | | | |

NOTES:
[1]MDA = methylene dianiline
[2]m-PDA = metaphenylene diamine
[3]NMA = nadic methyl anhydride
[4]BDMA = benzyldimethylamine
[5]Equivalents per equivalent weight of epoxide
[6]Heat Distortion Temperature.

It will be recognized by those knowledgeable in the art that the combination of HDT and flexural properties found for the optimum amount (0.5 equivalent) of m-PDA (formulation 535) was truly outstanding for an epoxy resin. It will be seen that use of each of the three curing agents in amounts greater than those giving the highest HDT's resulted in substantially better flexural properties without exacting too great a drop in HDT values.

Example III (Not an example, per se, of the present invention)

Preparation of product consisting essentially of tetra(methoxymethyl) bisphenol A (the balance being tri(-methoxymethyl) monomethylol bisphenol A).

300 Grams of bisphenol A was placed with 600 ml water in a 2-liter, 3-necked flask and stirred while 210.5 grams of 50% aq. NaOH was added. The warm mixture was cooled to 25° C. and 438 grams of formalin was stirred in. The mixture was heated, with stirring, to 40° C. and then exothermed to 46°; the temperature was restored to 40° C. and maintained at that level for a total reaction time of 7 hours. The reaction mixture stood at room temperature for two days and then was neutralized with 825 ml of 3N HCl. It was made slightly alkaline again, then slightly acid with HOAc. After chilling, to thicken the resin, the aqueous phase was poured off.

125 Grams of the resin (tetramethylol bis-phenol A) was diluted with methanol and the mixture stripped to yield a water-free retain sample. The rest of the resin was taken up in 1 liter of methanol, dried overnight over Drierite and filtered, using Filter-Aid. The filtrate was placed in a 3-liter, 3-necked flask and stirred while 10 ml of c. HCl was added. The mixture was stirred and refluxed for 10 hours, allowed to stand 3 days at room temperature, neutralized with NaHCO$_3$ and filtered. When most of the excess methanol was stripped off, the residual mixture separated into a resin phase and an aqueous phase—a brine. The brine was removed and stripping of the resin completed in a rotary evaporator. The stripped resin weighed 343 grams and gave strong phenolic —OH and —OCH$_3$ infrared absorptions. Upon analysis, the methoxyl content was found to be 26.6% (vs 30.7% for the desired tetra-(methoxymethyl) derivative. This corresponds approximately to an average —CH$_2$OH to —CH$_2$—OCH$_3$ conversion of about 87%, i.e., to an average of about 3.5 out of four methylol groups per molecule having been converted to methoxymethyl groups.

The latter product is an eminently suitable intermediate for the preparation of epoxy novolacs of the present invention.

Example IV

Preparation of novolacs by method affording better control of exotherms, followed by epoxidation.

The methods of novolac preparation described earlier herein are preferred for small scale preparations but do not permit sufficiently reliable control of the initial exotherm in large scale operations. The following "continuous addition" method—which was not invented by the present applicant—affords more positive temperature control and is therefore preferred for larger scale preparations, even though it results in a somewhat higher proportion of higher molecular weight oligomers in the novolac product. (More conventional methods of limiting heat evolution resulted in substantially higher molecular weights.)

A.

A solution of 340 grams (0.98 mole) of preformed tetramethylol bisphenol A (which had been kept in a freezer) and 2756 grams of phenol (29.3 moles; 7.5 molecules per methylol group) was made up. 900 Grams of this solution and 25 ml of c. HCl were stirred together in a 5-liter, round-bottom, 3-neck flask and heated. When the solution reached a temperature of 40° C., an exotherm to 75° occurred. Heating was continued and the temperature brought to and maintained thereafter in the range of 105±5° C. After 15 minutes at that temperature, anhydrous HCl gas was introduced to saturation. The balance of the tetramethylol bis A/phenol solution was then added in 500 ml aliquots at an average rate of about 25 ml per minute, the reaction mixture being resaturated with HCl after each aliquot had been added. After the final addition, the temperature was held at 105° C. for 90 minutes. The acid and water remaining in the mixture and the unconverted phenol were removed by stripping in a roto-evaporator under reduced pressure, followed by steam stripping of the residue.

Analysis of the novolac product by GPC (gel permeation chromatography) showed that it consisted of about 85% of monomer and about 15% of somewhat higher molecular weight species. The equivalent weight of the novolac (grams per phenolic hydroxyl) was 151 (versus about 110 for the ideal, 6 functional novolac of formula (2) herein.

B.

The novolac was epoxidized in the following manner. 69.9 Grams of the novolac is dissolved in 546 grams of epichlorohydrin (7 mols per phenolic OH) and 0.7 grams of BTMAC coupling-catalyst added. The solution is refluxed 2.5 hours and cooled to ambient temperature. 52 Grams of 25% aq. NaOH is added and the mixture stirred 1 hour at ambient temperature. Water and unconverted "epi" are removed by distillation in vacuo. The residue is dissolved in 70 grams of 75/25 MEK/toluene and heated to 60° C. Another 52 grams of 25% NaOH is then added at 60° C. in one hour and the reaction mixture stirred another hour at 60° C. More MEK/toluene is added in an amount equal to twice the weight of the novolac charged and half that amount of water is added, with stirring. Phase disengagement is permitted and the aqueous phase removed. The organic phase is dried (as with MgSO$_4$), mixed bentonite (20%; to remove BTMAC) and filter-aid, filtered and stripped.

The epoxide (nominally 6-functional, poly-glycidyl ether) had an EEW of 179 (vs. 165 theoretical). The HDT values obtained when this epoxide was cured 1:1 with each of two different curing agents are given in Table III following. Also included in the Table, for comparison, are the HDT values obtained with each of four different curing agents for a similar epoxide made essentially by the procedure of Example I but at a phenol/methylol ratio of 7.5 to 1 and epi/phenolic OH ratio of 7 to 1.

C.

A novolac was prepared essentially in the manner of Example IVA but employing o-cresol as the methylol-reactive phenol and in a ratio of 5 molecules per methylol group. It was epoxidized in the manner of Example IVB but with an epi/OH ratio of 10:1. HDT values of the epoxide, cured 1:1 and 0.7:1 with MDA (methylene dianiline), are included in Table III. Also included, for comparison, is an HDT value for the commercial 6-functional epoxy resin, "ECN-1280" (registered tradename; Ciba-Geigy, Epoxy Cresol Novolac) cured 1:1 with nadic methyl anhydride (NMA)+2% BDMA (benzyl dimethyl amine).

With regard to the HDT values in Table III, it should be noted that these were obtained with microsized specimens in a duPont TMA (Thermal Mechanical Analyzer)—which gives generally lower (but not more "correct") values than those determined with the older type macro size specimens in ASTM Method D648, the method by which the values given in Table II were obtained.

epoxy novolac made by the continuous addition method. It will also be seen that the cresol-derived epoxy novolac, cured with the same curing agent (MDA, 1:1), had a substantially higher HDT than the phenol-derived epoxy novolac, even though the cresol novolac was made by the continuous addition method and at a lower "phenol" to methylol ratio.

UTILITIES

More specific end uses contemplated for the present novolac epoxides are: for the lower molecular weight products, in adhesives, laminates and potting compounds; and for the higher molecular weight products, in molding compounds and powder coatings.

The epoxides of the present invention may of course be employed for various purposes in admixture with other epoxides, such as those derived from mono- or dihydric phenols or with polynuclear polyphenols such as phenol/formaldehyde novolacs, bisphenol/formaldehyde novolacs, or $C_1$–$C_6$ alkanes or alkenes substituted with from two to four hydroxyphenol groups. Such epoxide mixtures may be made by blending the separately-preformed epoxides or by epoxidizing mixtures of the novolacs disclosed herein with other phenols, polyphenols, etc., as above indicated.

What is claimed is:

1. An epoxy novolac consisting at least partially of a monomeric, polynuclear polyglycidyl ether of the formula:

TABLE III

| | HDT VALUES FOR SIX-FUNCTIONAL NOVOLAC EPOXIDES | | | | | | |
|---|---|---|---|---|---|---|---|
| NOVOLAC MADE FROM | φOH/ METHYLOL | epi/ Ar—OH | EEW | CURING AGENT | RATIO | CURE SCHEDULE HRS/°C. | HDT- (TMA) |
| Phenol; by method of Ex. I | 7.5 | 7 | 179 | NMA + 2% BDMA | 1:1 | 2/100 + 18/180 | 159° C. |
| " | " | " | " | DADS | 1:1 | 2/100 + 18/180 + 2/200 | 178 |
| " | " | " | " | NMA + 2 + BDMA | 1:1 | 2/90 + 4/165 | 122 |
| " | " | " | " | MDA | 1:1 | 2/90 + 4/165 | 195 |
| Phenol; by "continuous addition" method (Ex. IVA) | 7.5 | 7 | 192 | NMA + 2% BDMA | 1:1 | 2/100 + 18/180 | 135 |
| | | | | m-PDA | 1:1 | 2/85 + 10/150 | 185 |
| Cresol; by "continuous addition" | 5 | 10 | 249 | MDA | 1:1 | 2/100 + 18/180 | 220 |
| | | | | | 0.7:1 | 18/180 | 200 |
| ECN-1280 (Purchased) | | | 226 | NMA + 2% BDMA | 1:1 | 2/100 + 18/180 | 194 |

NOTES:
NMA = Nadic Methyl Anhydride
DADS = Diamino Diphenyl Sulfonate
BDMA = Benzyl Dimethyl Amine
MDA = Methylene Dianiline
PDA = Phenylene Diamine It will be seen from the data in Table III that the epoxidized novolac made from phenol by the method of Example I, when formulated with the same amount of the same curing agent (NMA/BDMA), gave a higher HDT than the otherwise comparable, higher EEW -continued

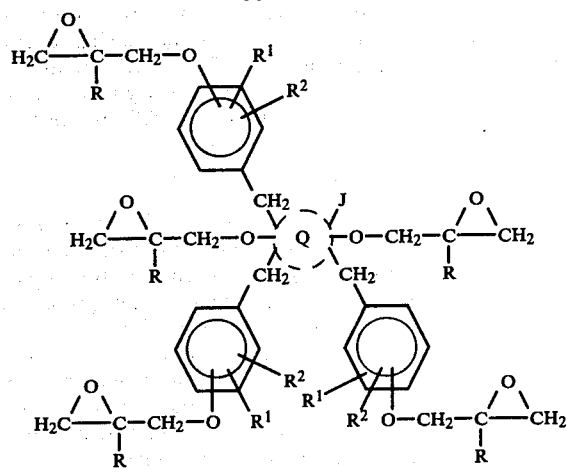

wherein:
R is H or CH₃,
R¹ is H, a $C_1$-$C_{20}$ alkyl, alkenyl, cycloalkyl, cycloalkenyl, aralkyl, aralkenyl, aryl, alkaryl, alkenylaryl, alkoxy or alkenyloxy group or a halo or nitro group, independently in each occurrence,
R² is H or OH, independently in each occurrence,
J is H, an R¹ group as above-defined or is a fourth

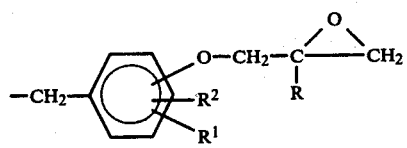

group, and
Q is the residue of a poly(methylol and/or alkoxy) difunctional phenol of either of the following formulas:

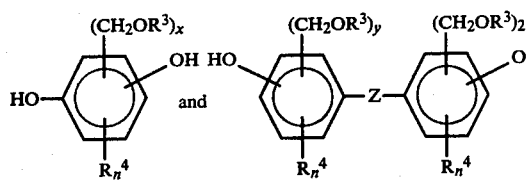

in which R⁴ is defined as is R¹ above, x is 3 or 4, n is 0 or 1, y is 1 or 2, —Z— is a valence bond, a $C_1$-$C_4$ alkylene or alkenylene group, or a =C(CF₃)₂, —CO—, —O—, —S—, —SO— or —SO₂— group and R³—independently in each occurrence is H or a $C_1$-$C_{30}$ alkyl, aralkyl or cycloalkyl group,
the balance, if any, of said novolac consisting of oligomeric species derivable from the acid-catalyzed reaction of a methylol- or methoxymethyl-reactive phenol of the formula

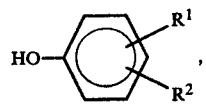

with a poly(methylol and/or alkoxymethyl)difunctional phenol,
R¹, R² and the latter difunctional phenol being as defined earlier in this claim.

2. The epoxy novolac of claim 1 consisting essentially of the hexaglycidyl ether of a polyphenol of the formula

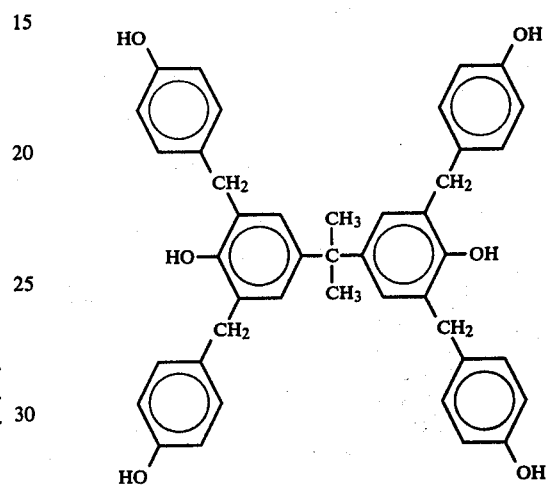

3. The epoxy novolac of claim 1 consisting essentially of the hexaglycidyl ether of a polyphenol of the formula:

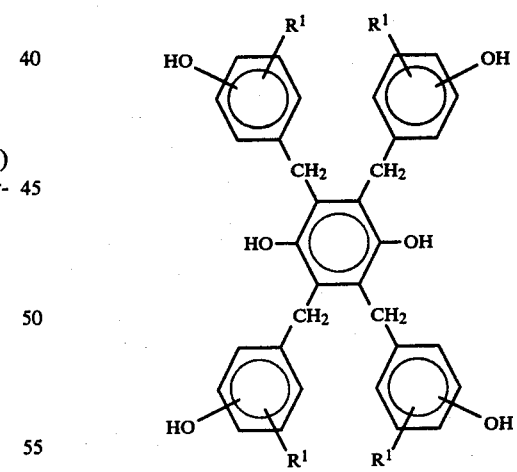

wherein R¹ is H, CH₃ or p-OH, independently in each occurrence.

4. The epoxy novolac of claim 1 in admixture with an epoxidized dihydric mononuclear phenol or polynuclear polyphenol of a formula other than that given in claim 1.

5. The epoxy novolac of claim 3 in which R¹ is CH₃, in all occurrences.

6. The epoxy novolac of claim 3 in which R¹ is p-OH, in all occurrences.